United States Patent [19]

Kirsch

[11] Plant 4,604

[45] Oct. 28, 1980

[54] LILY NAMED STAR FIRE

[75] Inventor: Ted T. Kirsch, Myrtle Point, Oreg.

[73] Assignee: Sun Valley Bulb Farms, Inc., Myrtle Point, Oreg.

[21] Appl. No.: 62,413

[22] Filed: Jul. 30, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new lily plant variety of the chalice-type Asiatic hybrid particularly distinguished by the brilliant orange-red coloring of its five to six inch diameter generally cup-shaped flowers which are borne in an umbellate arrangement on short, strong stems and strong, upright pedicels, usually with one or two buds or flowers on each pedicel, and by its short and stocky growth habit with abundant foliage.

1 Drawing Figure

BACKGROUND OF THE NEW PLANT

My new lily originated as a seedling of unknown parentage discovered by me while growing at my nursery at Arcata, Calif. The short and stocky growth habit and its bright upright flowers led me to propagate this plant for further study of its growth and handling characteristics. I propagated this new plant through several successive generations, by means of scales, and I found that this new plant had several meritorious advantages and distinctive characteristics which would make it a valuable addition for the commercial field of pot plant lily culture. Asexual propagation of this new variety through successive generations at Arcata, Calif., has also shown that its distinctive characteristics hold true from generation to generation and appear to be firmly fixed.

DESCRIPTION OF THE DRAWING

This new variety of lily plant is illustrated by the accompanying full color photographic drawing, which shows a full grown and blooming pot plant in the upper view and a close-up view of a fully opened bloom in the lower view, the color rendition being as nearly true as can be reasonably obtained by conventional photographic procedures.

DESCRIPTION OF THE NEW PLANT

The following is a detailed description of this new variety of Asiatic hybrid lily as observed at Arcata, Calif., with color designations according to the R.H.S. Colour Chart published by The Royal Horticultural Society of London, England, and developed with collaboration of The British Colour Council.

THE PLANT

Origin: Seedling.
Parentage: Unknown.
Classification:
*Botanic.*—Asiatic hybrid, chalice-type.
*Commercial.*—Pot plant lily.
Form: Tall, single stem arising from each bulb.
Height: About 12 to 18 inches, depending upon the size of the bulb.
Growth: Sturdy and upright with excellent strength.
Cane size: The stems grow from about ¼ inch diameter at the base when at a height of about 1 foot to about ½ inch base diameter for plants reaching a height of 18 inches.
Foliage: Quantity — abundant.
*Size of leaf.*—Stem leaves — from about 4 inches long and ½ inch wide at the middle of the plant to about 2 inches long and ¼ inch wide at the top of the plant.
*Leaves at flower cluster.*—Number: three. Size: about 1½ to 2½ inches long and about ½ to 1 inch wide.
*Shape of leaf.*—Lanceolate.
*Texture.*—Leathery.
*Aspect.*—Smooth and somewhat glossy.
Stem bulblets (under ground):
*Occurrence.*—4 to 12 on each healthy, normal plant at digging time.
*Size.*—About ¼ to 1 inch in diameter.
*Color.*—White.
Bulbs:
*Size.*—About 1 to 3 inches in diameter.
*Color.*—White.

THE BUD

Form: Elongate, oblong with retuse apex.
Size: Averaging 2 to 3 inches long and about ½ to 1 inch in diameter.
Opening: Normal, with tertiary and secondary buds opening successively.
Color: Red at the tip of the bud, fading to red-orange at the base when sepals first divide and petals begin to unfurl.
Surface aspect: Pubescent with white hairs about 1/16 inch long.
Pedicel: Strong and generally upright and angled about 30° from vertical.
*Length.*—1⅞ to about 2½ inches.
*Color.*—Light green.
*Aspect.*—Slightly pubescent with white hairs about 1/16 inch long.
Number of buds: 1 or 2 on each pedicel, depending upon the size of the bulb.

THE FLOWER

Blooming habit: Annually, blooming profusely in June.
Size of flower: Medium, averaging about 5 to 6 inches in diameter and about 1 to 1½ inches in depth.

Borne: From the larger bulbs, the inflorescence has a raceme arrangement for the first 2 to 6 pedicels, each of which has only 1 bud and then at the top, the inflorescence breaks into an umbellate cluster of 2 to 3 pedicels each having 1 bloom. Generally the size of the bulb and its culture care will determine the number of blooms and buds to be found on any given inflorescence. From somewhat smaller bulbs, this lily may have 6 to 8 blooms open at one time, one on each pedicel, and 1 to 2 open at the top umbel cluster.

Shape: The flower is generally cup-shaped with uniformly spaced petals in star arrangement with the very tips of the petals folding outwardly and curving back and under.

Petalage: Normal, 3 sepals and 3 petals.

*Form.*—Oval, with retuse apex and prominent nectariferous grooves and a center furrow bisecting each petal longitudinally.

*Size.*—About 2 inches wide and 3 inches long with edges entire.

*Color.*—Upper side — upon opening, the petals have a background color between RHS 34A and 34B with a white nectariferous groove which extends into a red area of RHS 44A in the center of the petal beyond the end of the nectariferous groove. Although not prominent, the entire petal area, including one inch of the tip, is profusely covered with very tiny spots. Under side — dark red-orange 35A, with the outer edges of RHS 34A. Aspect — slightly pubescent.

*Papillae.*—4 to 8 in number present on petals.

*Texture.*—Leathery.

*Aspect.*—Velvety.

Fragrance: None.

Discoloration: Color holds up very well as blossom matures.

Effect of weather: Generally the flower is not affected by wet weather, but ages as the temperature rises.

Persistence: The flowers tend to hang on and dry.

Lasting quality: Excellent; 3 to 6 weeks on plant, depending on size of bulb and temperature, and 10 days to 2 weeks as a cut flower.

REPRODUCTIVE ORGANS

Stamens:

*Anthers.*—6 in number. Arrangement: orderly around the pistil. Length: about ½ inch. Color: pale orange to red at the tip.

Filaments: About 2 inches long.

Pistils:

*Number.*—One.

*Style.*—Length: about 2 inches. Color: pale orange.

*Stigma.*—Color — pale orange to red at the style.

Ovary: Classified as a schizocarp, about 1½ to 2 inches long and about one inch in diameter, dehiscing into thirds and containing 6 rows of seeds of the normal shape.

It is to be noted that this variety Star Fire is very similar to the variety Crimson Sun (application copending) in many respects. The foliage of Crimson Sun, however, is much glossier than that of Star Fire and is not as firmly attached to the stem as is the foliage of Star Fire.

Upon opening of the buds, the main petal color is about the same (RHS 34A) for both Star Fire and Crimson Sun. There are, however, a number of distinctive color differences between the two flowers. Star Fire is a darker shade of red, RHS 44A, in the center of the petal than Crimson Sun, which is the color of RHS 34A. The petals of Star Fire are approximately one-quarter to one-half inch wider than those of Crimson Sun and the flower of Star Fire is less cupped than that of Crimson Sun. Also, Crimson Sun fades to a rust-orange as it matures while Star Fire maintains its deep red coloring until the flower ages and dies. It is noted that with respect to the reproductive organs, the stigma of Crimson Sun stands above the anthers while the stigma of Star Fire is even with the anthers.

With respect to growth habit, abundance of foliage, rapid asexual reproduction rate and the extremely quick and consistently high quality of forcing as a pot plant, both Star Fire and Crimson Sun have the same characteristics and advantages.

I claim:

1. The new and distinctive variety of Asiatic hybrid lily plant substantially as herein shown and described, characterized by the color, form and arrangement of its brilliant red flowers and by its short and stocky growth habit and abundant foliage.

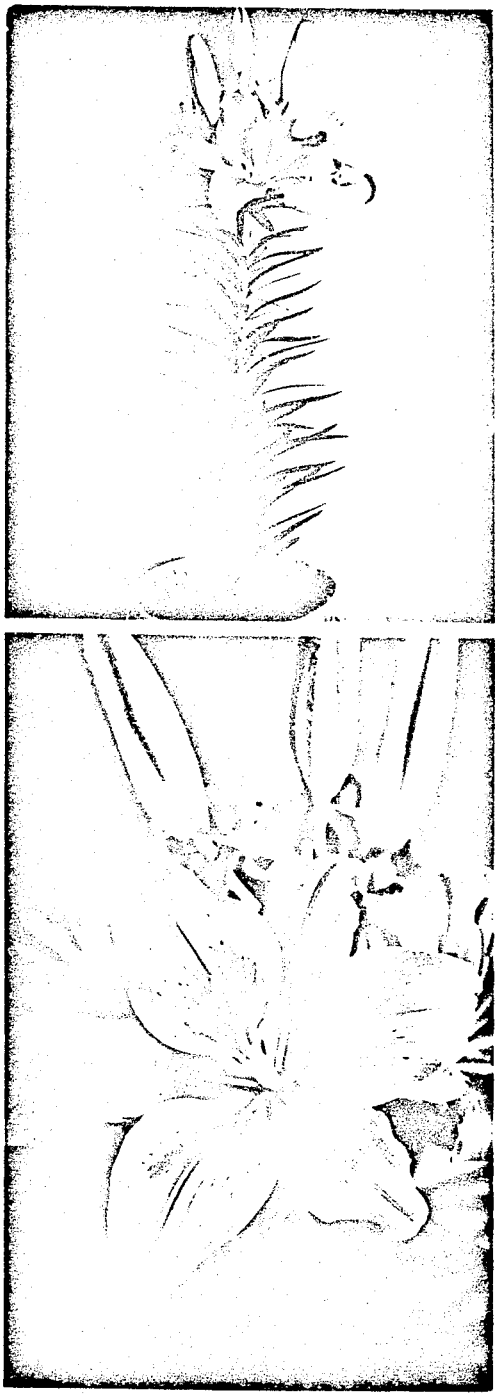

* * * * *